US012636092B1

(12) United States Patent
Winston et al.

(10) Patent No.: US 12,636,092 B1
(45) Date of Patent: May 26, 2026

(54) MEDICAL DEVICE INSERTER INSTRUMENTS WITH RETRACTABLE COUPLING ELEMENTS AND METHODS OF USING THE SAME

(71) Applicant: Carlsmed, Inc., Carlsbad, CA (US)

(72) Inventors: Jeremy Winston, San Diego, CA (US); Jade Sommers, San Diego, CA (US)

(73) Assignee: Carlsmed, Inc., Carlsbad, CA (US)

( * ) Notice: Subject to any disclaimer, the term of this patent is extended or adjusted under 35 U.S.C. 154(b) by 0 days.

(21) Appl. No.: 18/793,269

(22) Filed: Aug. 2, 2024

Related U.S. Application Data

(60) Provisional application No. 63/530,427, filed on Aug. 2, 2023.

(51) Int. Cl.
| | |
|---|---|
| *A61B 34/20* | (2016.01) |
| *A61B 17/88* | (2006.01) |
| *A61B 17/00* | (2006.01) |

(52) U.S. Cl.
CPC .............. *A61B 34/20* (2016.02); *A61B 17/88* (2013.01); *A61B 2017/00407* (2013.01); *A61B 2017/00477* (2013.01); *A61B 2017/00862* (2013.01); *A61B 2017/00991* (2013.01); *A61B 2034/2051* (2016.02); *A61B 2034/2055* (2016.02); *A61B 2034/2068* (2016.02)

(58) Field of Classification Search
CPC ..... A61B 17/88; A61B 17/8841; A61B 34/10; A61B 34/20; A61F 2/4611
See application file for complete search history.

(56) References Cited

U.S. PATENT DOCUMENTS

| | | | |
|---|---|---|---|
| 4,704,686 | A | 11/1987 | Aldinger |
| 6,772,026 | B2 | 8/2004 | Bradbury |
| 7,174,282 | B2 | 2/2007 | Hollister et al. |

(Continued)

FOREIGN PATENT DOCUMENTS

| | | |
|---|---|---|
| CN | 104318009 A | 1/2015 |
| CN | 104353121 A | 2/2015 |

(Continued)

OTHER PUBLICATIONS

Endo, Kenji et al. "Measurement of whole spine sagittal alignment using the SLOT radiography of the SONIALVISION safire series clinical application." Medical Now, No. 78; Aug. 2015, 4 pages.

(Continued)

*Primary Examiner* — Si Ming Ku
(74) *Attorney, Agent, or Firm* — Perkins Coie LLP

(57) ABSTRACT

The present technology includes inserter instruments for use with medical implant procedures. The inserter instruments can include features that are expected to enable the inserter instruments to be accurately registered with off-the-shelf or conventional surgical navigation systems. For example, the inserter instruments can include a retractable implant coupling element. The retractable implant coupling element can be selectively transitioned between (a) a first configuration in which the implant coupling element extends past a distal end of a shaft of the inserter, and (b) a second configuration in which the implant coupling element is retracted inside the shaft such that it is flush with, or positioned proximally of, the distal end of the shaft.

11 Claims, 11 Drawing Sheets

400

402 — Retracting an implant coupling element on the inserter instrument into a shaft of the inserter instrument 404 — Registering the inserter instrument with a surgical navigation system while the implant coupling element is in the retracted configuration 406 — Unretracting the implant coupling element until at least a portion of the implant coupling element extends distally past a distal end of the shaft 408 — Coupling a medical implant to the implant coupling element while the implant coupling element is in the unretracted configuration 410 — Implanting the medical implant in a patient using the inserter instrument and the surgical navigation system

(56) References Cited

U.S. PATENT DOCUMENTS

| | | |
|---|---|---|
| 7,799,077 B2 | 9/2010 | Lang |
| 8,246,680 B2 | 8/2012 | Betz |
| 8,265,949 B2 | 9/2012 | Haddad |
| 8,275,594 B2 | 9/2012 | Lin |
| 8,337,507 B2 | 12/2012 | Lang |
| 8,394,142 B2 | 3/2013 | Bertagnoli |
| 8,457,930 B2 | 6/2013 | Shroeder |
| 8,556,983 B2 | 10/2013 | Bojarski et al. |
| 8,644,568 B1 | 2/2014 | Hoffman |
| 8,735,773 B2 | 5/2014 | Lang |
| 8,758,357 B2 | 6/2014 | Frey |
| 8,775,133 B2 | 7/2014 | Schroeder |
| 8,781,557 B2 | 7/2014 | Dean |
| 8,843,229 B2 | 9/2014 | Vanasse |
| 8,855,389 B1 | 10/2014 | Hoffman |
| 8,870,889 B2 | 10/2014 | Frey |
| 9,198,678 B2 | 12/2015 | Frey et al. |
| 9,208,558 B2 | 12/2015 | Dean |
| 9,445,907 B2 | 9/2016 | Meridew |
| 9,542,525 B2 | 1/2017 | Arisoy et al. |
| 9,642,633 B2 | 5/2017 | Frey et al. |
| 9,693,831 B2 | 7/2017 | Mosnier et al. |
| 9,707,058 B2 | 7/2017 | Bassett |
| 9,775,680 B2 | 10/2017 | Bojarski et al. |
| 9,782,228 B2 | 10/2017 | Mosnier et al. |
| 9,993,341 B2 | 6/2018 | Vanasse |
| 10,292,770 B2 | 5/2019 | Ryan |
| 10,390,958 B2 | 8/2019 | Maclennan |
| 10,646,258 B2 | 5/2020 | Donner et al. |
| 2017/0135706 A1 | 5/2017 | Frey et al. |
| 2017/0143831 A1 | 5/2017 | Varanasi et al. |
| 2017/0220740 A1 | 8/2017 | D'Urso |
| 2018/0303552 A1 | 10/2018 | Ryan |
| 2022/0346844 A1* | 11/2022 | Dewey .................. A61B 90/39 |

FOREIGN PATENT DOCUMENTS

| | | |
|---|---|---|
| CN | 204468348 U | 7/2015 |
| CN | 105796214 A | 7/2016 |
| CN | 110575289 A | 12/2019 |
| EP | 3120796 A1 | 1/2017 |
| WO | 2014180972 A2 | 11/2014 |
| WO | 2016172694 A1 | 10/2016 |
| WO | 2019112917 A1 | 6/2019 |

OTHER PUBLICATIONS

Materialise Mimics, "Efficiently turn scans into accurate virtual 3D models," Retrieved on Nov. 1, 2019 at www. materialize.com/en/medical/software/mimics, 1 page.
Pimenta, Dr. Luiz, "Current Surgical Strategies to Restore Proper Sagittal Alignment," Journal of Spine 2015, vol. 4, Issue 4, 2 pages.
U.S. Appl. No. 15/958,409 for Rya, filed Apr. 21, 2017.

* cited by examiner

MEDICAL DEVICE INSERTER INSTRUMENTS WITH RETRACTABLE COUPLING ELEMENTS AND METHODS OF USING THE SAME

CROSS-REFERENCE TO RELATED APPLICATION(S)

The present application claims priority to U.S. Provisional Application No. 63/530,427, filed Aug. 2, 2023, the disclosure of which is incorporated by reference herein in its entirety.

TECHNICAL FIELD

The present disclosure is generally related to medical care, and more particularly to delivery instruments for implanting a medical device during a surgical procedure, and methods of using the same.

BACKGROUND

Medical procedures that involve implanting a medical device within a patient often utilize Computer Assisted Navigation ("navigation") to provide a surgeon or other healthcare provider with real-time information about the location of the medical device during the surgical procedure. To ensure that a surgical navigation system is providing accurate positional information to the surgeon, the inserter instrument used to implant the medical device is typically registered to the surgical navigation system prior to performing the surgical procedure. Registration is often performed by registering a first set of fiducial markers on the inserter instrument to a second set of fiducial markers located on patient arrays in the operating room. The distance between the first set of fiducial markers and the second set of fiducial markers can then be tracked in real-time to track the surgical field intraoperatively. Accordingly, the surgical navigation system typically provides accurate navigation only if it has been properly registered to the inserter instrument.

BRIEF DESCRIPTION OF THE DRAWINGS

The accompanying drawings illustrate various embodiments of systems, methods, and embodiments of various other aspects of the disclosure. Any person with ordinary skill in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

Figure 1A:
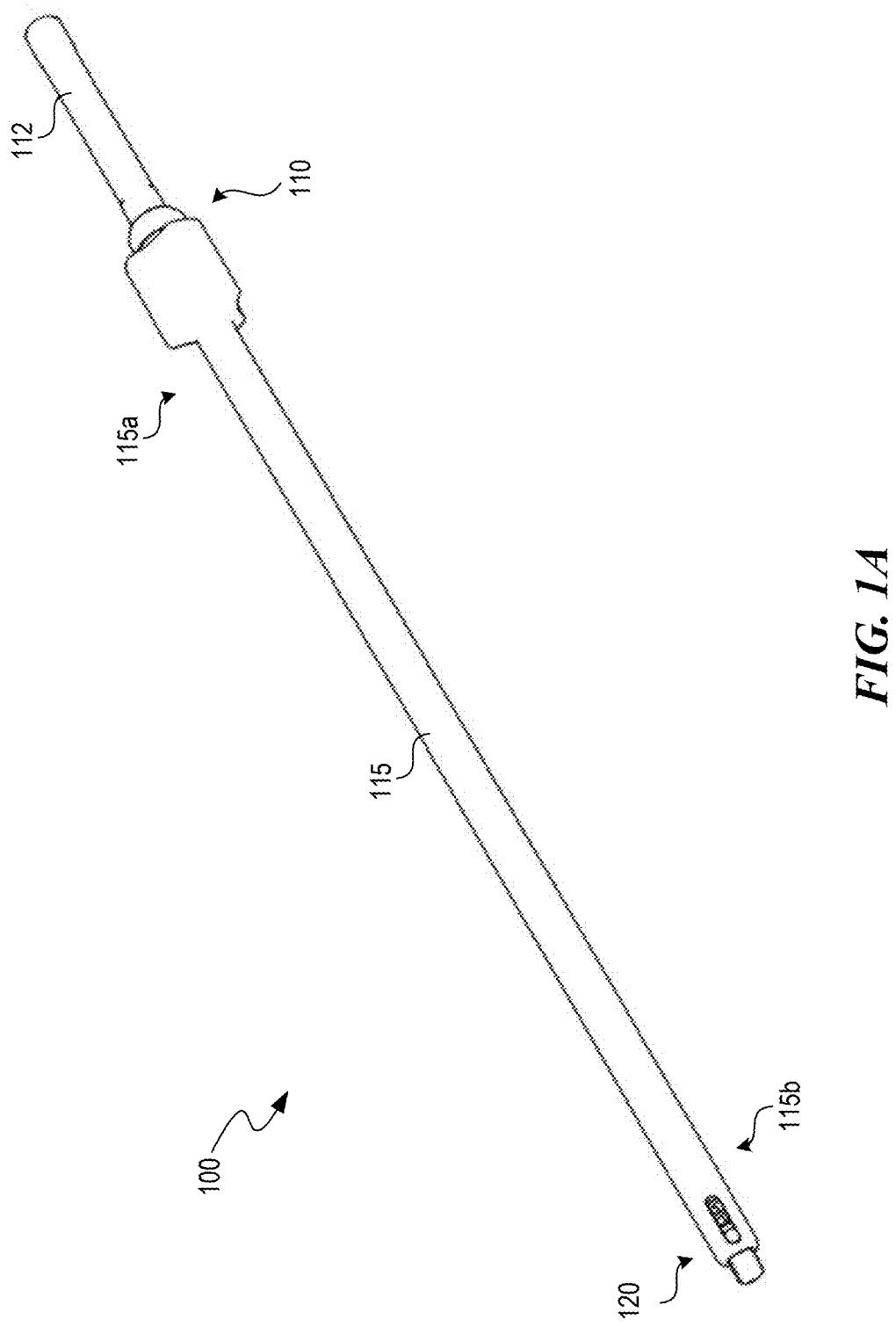
FIG. 1A is an isometric view of an inserter instrument configured in accordance with embodiments of the present technology.

The present technology is directed to inserter instruments and methods of using the same. Inserter instruments are releasably coupled to medical implants and used to deliver, position, and/or deploy the medical implant at a target location during a surgical procedure. To do so, inserter instruments typically have a male connection element at their distal end that can be releasably coupled to a corresponding female connection element on the medical implant. Because the male connection element extends at least partially into the medical implant, registering the end of the male connection element as the end of the inserter instrument to a surgical navigation system may create an offset between where the implant actually is, and where the navigation system "thinks" the implant is. As a result, it can be difficult to accurately register inserter instruments to surgical navigation systems. For example, the surgical navigation system generally must account for the length of the male connection element that will be inserted into the female connection element of the implant to ensure the correct location along the length of the inserter instrument is registered as the distal-most end of the instrument. In practice, this often limits surgical navigation systems to being used with instruments and implants provided by the same manufacturer as the surgical navigation system.

The inserter instruments described herein can include features that are expected to enable the inserter instruments to be accurately registered with off-the-shelf or conventional surgical navigation systems. For example, in many embodiments described herein the inserter instruments include a retractable implant coupling element. The retractable implant coupling element can be selectively transitioned between (a) a first configuration in which the implant coupling element extends past a distal end of a shaft of the inserter, and (b) a second configuration in which the implant coupling element is retracted inside the shaft such that it is flush with, or positioned proximally of, the distal end of the shaft so that it does not extend past the distal end of the shaft. The inserter instrument can be registered to a surgical navigation system when the implant coupling element is in the second configuration. As a result, the distal end of the shaft can be registered as the distal end of the inserter instrument. After registration is complete, the implant coupling element can be transitioned to the first configuration in which at least a portion of the implant coupling element is exposed. A medical device can then be coupled to the implant coupling element (e.g., via a threaded connection) such that the medical device is flush with the distal end of the shaft.

Accordingly, and without intending to be bound by theory, one expected advantage of the inserter instruments described herein is their compatibility with off-the-shelf or conventional surgical navigation systems. That is, the inserter instruments can be accurately registered to off-the-shelf surgical navigation systems, even though the inserter instruments include a male connection element that is inserted into a female connection element on the implant. As a result, hospitals, ambulatory surgical centers, and other healthcare providers can use existing surgical navigation system to provide navigation during medical implant procedures, without being limited to choosing between using specific implants made by the same manufacturer as their navigation system or performing the medical procedure without navigation.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

As used herein and in the appended claims, the singular forms "a," "an," and "the" include plural references unless the context clearly dictates otherwise.

As used herein in the context of inserter instruments, the term "proximal" generally refers to a direction toward an end of the inserter associated with the user/manipulator (e.g., toward the inserter handle that remains external to a patient during an implant procedure), and the term "distal" generally refers to a direction toward an end of the inserter associated with an implant (e.g., toward the portion of the inserter configured to be coupled to the implant).

Although the disclosure herein primarily describes systems and methods for treatment planning in the context of orthopedic surgery, the technology may be applied equally to medical treatment and devices in other fields (e.g., other types of surgical practice). Additionally, although many embodiments herein describe systems and methods with respect to implanted devices, the technology may be applied equally to other types of medical devices (e.g., non-implanted devices).

FIGS. 1A-1E illustrate an inserter instrument 100 ("the instrument 100") configured in accordance with embodiments of the present technology. As described in detail below, the instrument 100 can be a delivery instrument for surgically delivering, positioning, deploying, and/or implanting a medical implant. For example, in some embodiments the instrument 100 is an "interbody" inserter instrument that can be used by a surgeon to place an interbody implant device at a particular vertebral level within a patient's spine. Of note, and as described in detail below, the instrument 100 includes a retractable tip portion that enables the instrument 100 to transition between a first configuration in which it can be releasably coupled to a medical implant, and a second configuration in which it can be accurately registered to a surgical navigation system.

Referring first to FIG. 1A, which is an isometric view of the instrument 100, the instrument 100 includes an elongated shaft 115 ("the shaft 115") extending between a first (e.g., proximal) end portion 115$a$ and a second (e.g., distal) end portion 115$b$. In some embodiments, the shaft 115 is composed of a generally rigid material or blend of materials (e.g., steel, stainless steel, titanium, etc.). The instrument 100 further includes a proximal complex 110 at the proximal end portion 115$a$ of the shaft 115 and a distal complex 120 at the distal end portion 115$b$ of the shaft 115. The proximal complex 110 can include a handle 112 sized and shaped to permit a surgeon or other user to control the instrument 100 by grasping the handle 112.

Figure 1B:
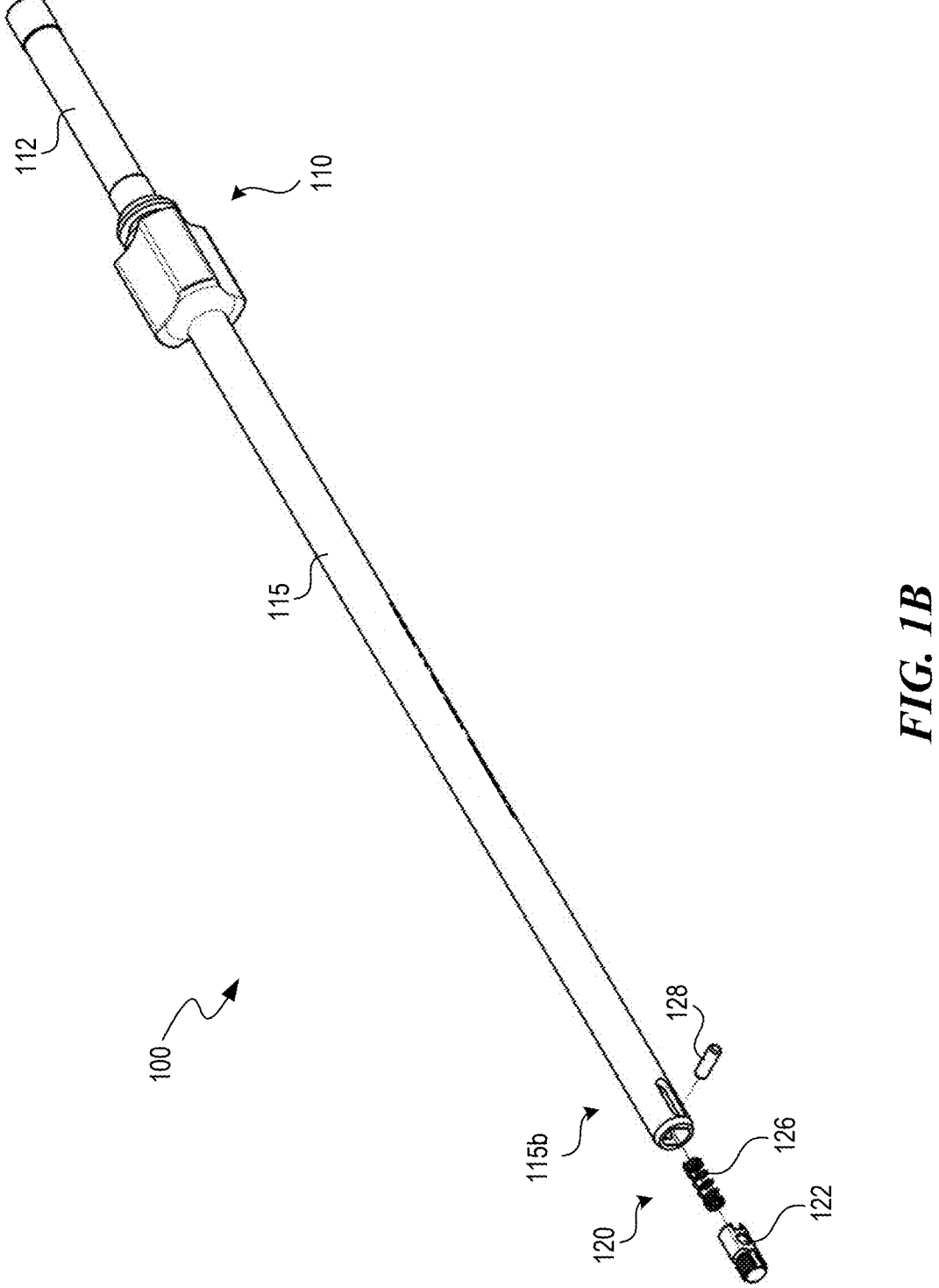
FIG. 1B is an exploded view of the inserter instrument of FIG. 1A.

The distal complex 120 can include one or more features sized and shaped to be releasably coupled to an implant (not shown in FIG. 1A). For example, as best shown in FIG. 1B, which is an exploded view of the instrument 100, the distal complex 120 can include an implant coupling element 122 sized and shaped to be releasably coupled to an implant (also not shown in FIG. 1B). The distal complex 120 can further include a spring 126 and a pin 128. As described in detail below, the implant coupling element 122 can be configured to slidably translate within the distal end portion 115$b$ of the shaft 115, e.g., by compressing the spring 126, thereby transitioning the distal complex 120 from the first configuration to and/or toward the second configuration (which may also be referred to herein as a "registration configuration" or a "retracted configuration"). Additional features regarding the distal complex 120 are described in detail below with reference to FIGS. 1C and 1D.

Figure 1C:
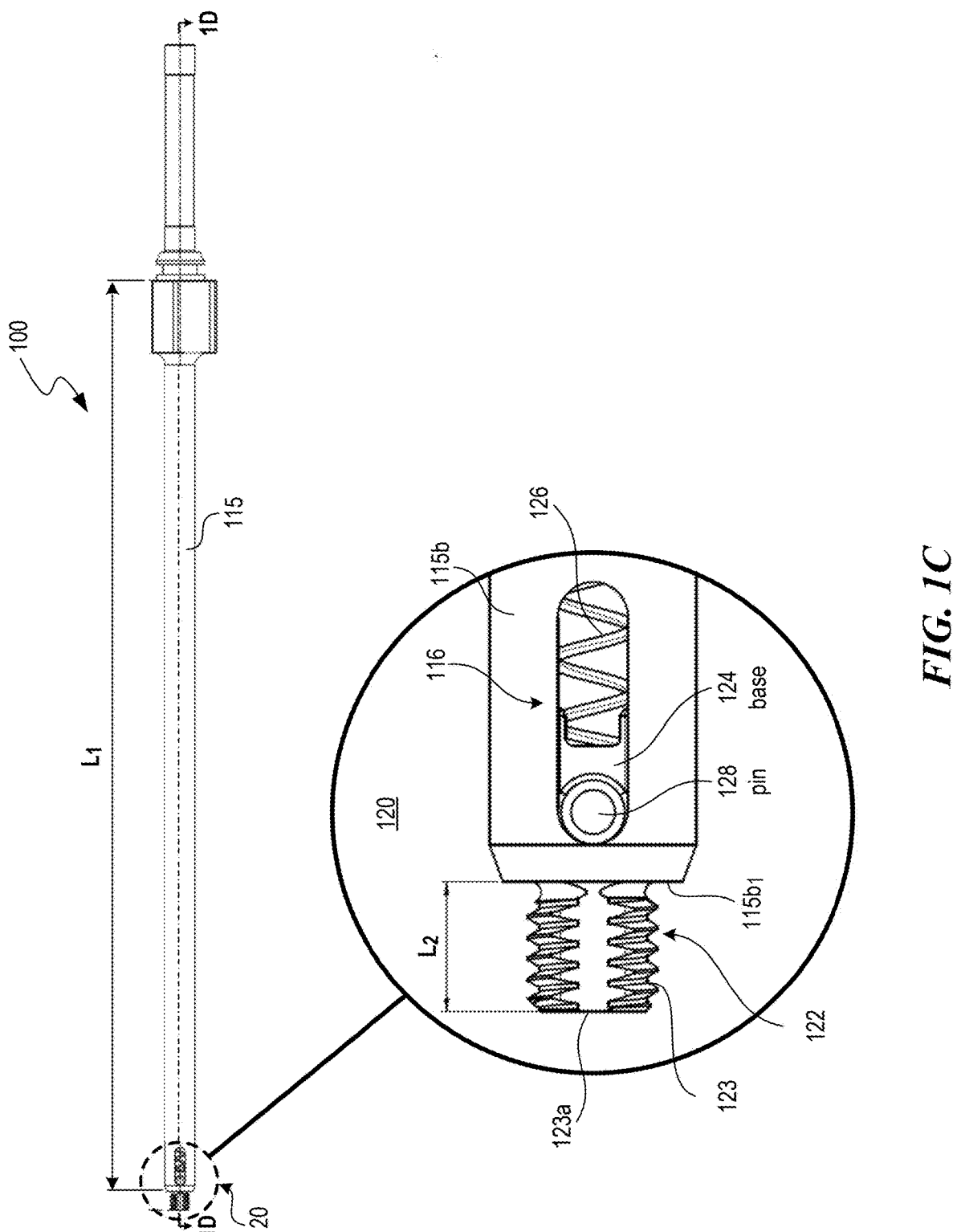
FIG. 1C is side view of the inserter instrument of FIG. 1A and includes an enlarged view of a distal complex of the inserter instrument.
Figure 1D:
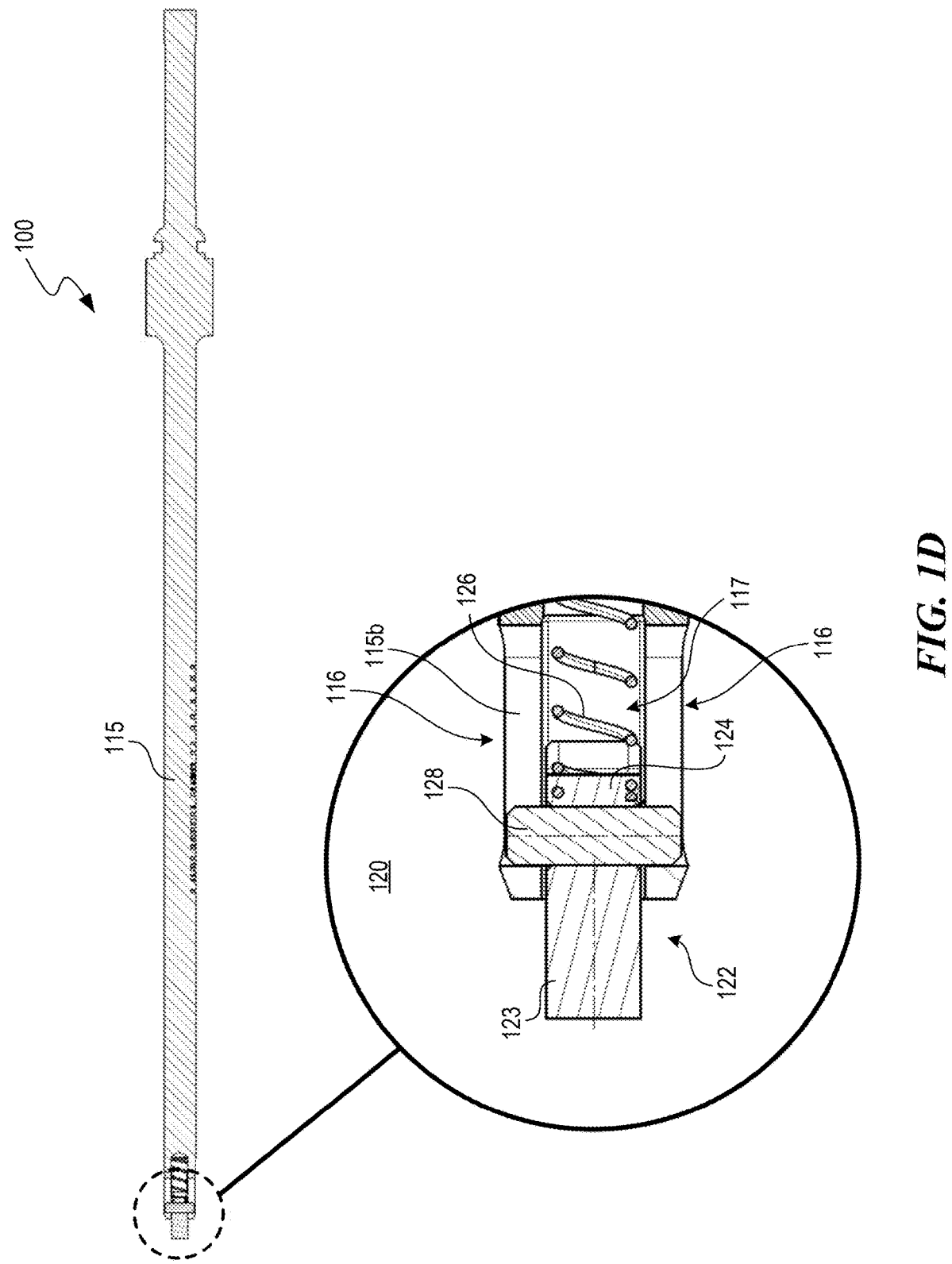
FIG. 1D is a cross-sectional view of the inserter instrument of FIG. 1A, including an enlarged cross-sectional view of the distal complex of the inserter instrument, taken along the lines indicated in FIG. 1C.

FIG. 1C is a side view of the instrument 100 of FIGS. 1A and 1B and includes an enlarged view of the distal complex 120. FIG. 1D is a cross-sectional side of the instrument 100 taken along the lines indicated in FIG. 1C, and further includes an enlarged cross-sectional view of the distal complex 120. Both FIGS. 1C and 1D illustrate the distal complex 120 in the first configuration in which the instrument 100 can be coupled to an implant. The first configuration can therefore also be referred to herein as a "delivery configuration," or an "expanded configuration."

Referring first to FIG. 1C, the shaft 115 can have a first length $L_1$. The first length $L_1$ can be based at least in part on the type of procedure and/or implant that the instrument 100 is to be used to perform/implant. For example, the first length $L_1$ can be based on a predicted insertion depth between a target insertion location at which the instrument 100 enters the patient and a target implant location at which the implant carried by the instrument 100 is to be implanted. As described in greater detail below with reference to FIG. 2A, the first length $L_1$ can also be a "registration length" that is based at least in part on a dimension of a different instrument that has a profile stored on a surgical navigation system. As one skilled in the art will appreciate, however, the first length $L_1$ of the shaft 115 can also be based off other factors, such as surgeon preference, manufacturing capabilities, shipping capabilities, cost, etc. In some embodiments, the first length $L_1$ is between about 15 cm and about 40 cm, or between about 15 cm and about 35 cm, or between about 20 cm and 30 cm, or about 25 cm. As shown in the cross-sectional view of FIG. 1D, the shaft 115 can be solid (as opposed to hollow) along all of, or substantially all of, the first length $L_1$. This may provide greater rigidity to the instrument 100, reduce manufacturing complexity, reduce manufacturing cost, and/or provide other advantages. In other embodiments, however, the shaft 115 can be hollow or at least partially hollow along the first length $L_1$.

Referring collectively to the enlarged portions of FIGS. 1C and 1D showing the distal complex 120, the implant coupling element 122 includes a base 124 and a threaded region 123 extending distally from the base 124. In the first configuration, the base 124 can be positioned within a hollow interior or lumen 117 (FIG. 1D) of the distal end portion 115b of the shaft 115, while the threaded region 123 can extend distally past a distal end 115b1 of the shaft 115. For example, in the first configuration and as shown in FIG. 1C, a distal end 123a of the threaded region 123 extends past the distal end 115b1 of the shaft 115 by a second length $L_2$, which can be between about 2 mm and about 2 cm, or between about 2 mm and about 1 cm, or between about 3 mm and about 8 mm, or between about 4 mm and about 6 mm, or about 5 mm. Thus, when in the first configuration, the threaded region 123 can be exposed and available to be attached to a corresponding bore hole on an implant, as described below with reference to FIG. 1E. The instrument 100 can therefore be designed such that the second length $L_2$ corresponds to a depth of the corresponding threaded receiving hole in the implant, as also described in greater detail below with reference to FIG. 1E. In some embodiments, the second length $L_2$ may be less than or greater than the depth of the corresponding threaded receiving hole in the implant. As also described in greater detail below, the implant coupling element 122 can be configured to translate proximally relative to the shaft 115 such that, in the second configuration, the threaded region 123 is positioned partially or fully within the shaft 115, and the second length $L_2$ is zero or substantially zero. The implant coupling element 122 can be composed of a generally rigid material or blend of materials (e.g., steel, stainless steel, titanium, etc.).

The spring 126 is positioned within the lumen 117 and extends proximally from the base 124 of the implant coupling element 122. In operation, the spring 126 can bias the coupling element 122 distally (e.g., toward the distal end 115b1 of the shaft 115), thereby biasing the distal complex 120 toward the first (delivery) configuration in which the threaded region 123 extends past the end 115b1 of the shaft 115. However, the distal complex 120 can be transitioned to the second configuration by imparting a proximally directed force on the implant coupling element 122, which compresses the spring 126 and causes the implant coupling element 122 to translate into the shaft 115. In some embodiments, the distal complex 120 can further include a retention mechanism (not shown) designed to counteract the biasing force of the spring 126 to temporarily and releasably retain the distal complex 120 in the second (retracted) configuration. Suitable retention mechanisms include, but are not limited to, hooks, latches, ratchets, or the like.

In some embodiments, the spring 126 can have a generally coiled, helical, or other suitable shape that can be elastically compressed. In such embodiments, the spring 126 can be composed of a metal or metal alloy that, based on its shape, provides a generally elastic response when mechanically compressed. Suitable materials include, but are not limited to, steel, stainless steel, titanium, superelastic nickel titanium, or the like. In other embodiments, the spring 126 does not have a traditional spring-like shape (e.g., the spring 126 can be a solid cylinder), and can instead be composed of an elastically compressible material. In yet other embodiments, the distal complex 120 can include other biasing elements in addition to, or in lieu of, the spring 126. For example, the distal complex 120 can have a scissor-jack mechanism, an accordion mechanism, or the like.

The pin 128 can be rotatably and translationally locked to the implant coupling element 122. The pin 128 can also extend at least partially through an axial slot 116 in the shaft 115. The pin 128 can be sized and shaped such that the slot 116 defines the range of motion of, or "track" for, the pin 128. For example, the pin 128 can be sized and shaped such that it can translate within the slot 116, but not rotate relative to the shaft 115. As a result, the pin 128 permits the distal complex 120 to slidably translate between the first (expanded) configuration and the second (retracted) configuration, while preventing or at least reducing an amount the implant coupling element 122 can rotate relative to the shaft 115.

As best shown in the enlarged portion of FIG. 1D showing the cross-section of the distal complex 120, the distal end portion 115b of the shaft 115 can include two slots 116 oriented on generally opposite sides of the lumen 177. The pin 128 can extend through both of the slots 116. In such embodiments, the pin 128 extends through an entire diameter of the shaft 115. Without intending to be bound by theory, having the pin 128 extend through slots 116 on opposing sides of the shaft 115 is expected to improve the positional control the pin 128 provides over the implant coupling element 122.

Although the distal complex 120 is described as being biased toward the first configuration by virtue of the spring 126, in other embodiments the distal complex 120 may be biased toward whichever configuration it currently occupies. In such embodiments, the distal complex 120 may be designed such that (a) the first configuration and the second configuration represent relatively low energy states for the distal complex 120, and (b) the distal complex 120 must pass through a relatively higher energy state to transition between the first configuration and the second configuration. In some embodiments, the relatively higher energy state can be provided by a mechanical feature such as a tooth, protrusion, ramp, ratchet, or the like. Alternatively, the pin 128 and the slot 116 can be omitted, and the implant coupling element 122 can be compressed into the shaft 115 and directed laterally such that the spring 126 biases the implant coupling element 122 against a biasing surface internal to the shaft 115. Regardless, if the distal complex 120 is in the first configuration, the distal complex 120 is biased toward remaining in the first configuration because an energy input is required to transition the distal complex 120 toward the second configuration. Likewise, if the distal complex 120 is in the second configuration, the distal complex 120 is biased toward remaining in the second configuration because an energy input is required to transition the distal complex 120 toward the second complex. Without intending to be bound by theory, biasing the distal complex 120 toward whichever position it occupies at any given time may improve the stability of, and control over, the position of the implant coupling element 122.

Further, although the foregoing describes transitioning the distal complex 120 between a first configuration and second configuration, in some embodiments the distal complex 120 can be retained at various incremental configurations between the first configuration and the second configuration (e.g., via a ratchet, sawtooth, or other suitable configuration). In such embodiments, the distal complex 120 can be selectively transitioned between the incremental configurations, which each incremental configuration providing a different "second length $L_2$" between the distal end 123$a$ of the threaded region 123 and the distal end 115$b_1$ of the shaft.

Figure 1E:
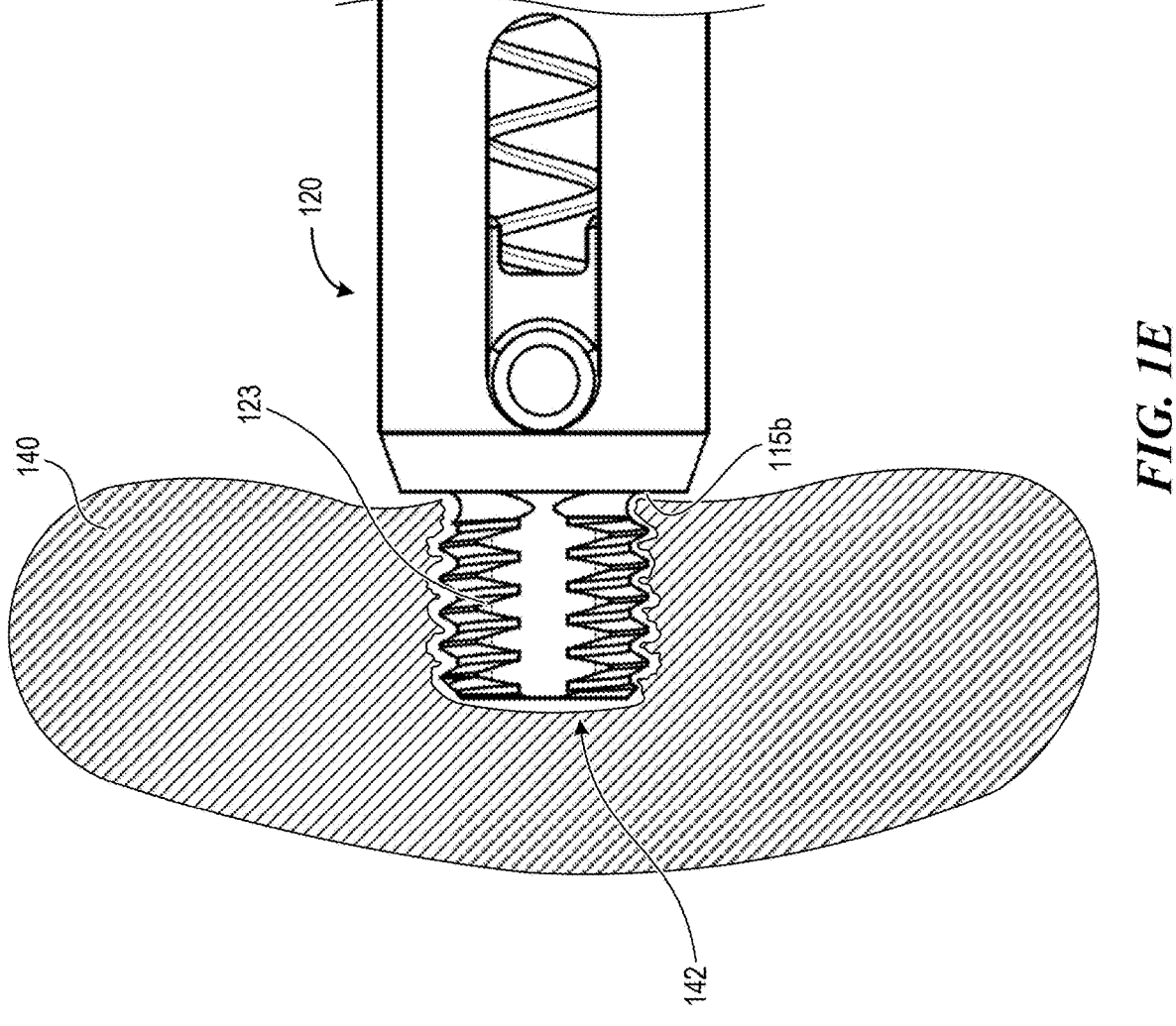
FIG. 1E illustrates the inserter instrument of FIG. 1A coupled to a medical implant configured in accordance with embodiments of the present technology.

An implant can be coupled to the instrument 100 when the distal complex 120 is in the first configuration. For example, FIG. 1E illustrates an implant 140 (shown in cross-section) coupled to the distal complex 120 of the instrument 100. More specifically, the implant 140 includes a threaded female coupling element 142 (e.g., a threaded hole or channel) sized and shaped to releasably receive the threaded region 123 of the instrument 100. Of note, the threaded female coupling element 142 has a depth that is equal to or greater than the length of the threaded region 123 (e.g., equal to or greater than the second length $L_2$ described with reference to FIG. 1C). Thus, when the implant 140 is coupled to the instrument 100, the threaded region 123 is positioned within the implant 140 and the implant 140 can sit flush with, or substantially flush with, the distal end 115$b1$ of the shaft 115. The implant 140 can be an orthopedic implant, expandable intervertebral cage, non-expandable cage, artificial disc, fixation plate, or the like. In some embodiments, the implant 140 can be a "patient-specific" implant having one or more features (e.g., size, shape, endplate topography, etc.) designed for a particular patient's anatomy. In such embodiments, the threaded female coupling element 142 can nevertheless be a "standard" size such that the instrument 100 can be used with such "patient-specific" implants with different dimensions, sizes, shapes, etc. In other embodiments, the instrument 100 can be designed specifically for use with a particular patient-specific implant, or class of patient-specific implants.

Figure 2A:
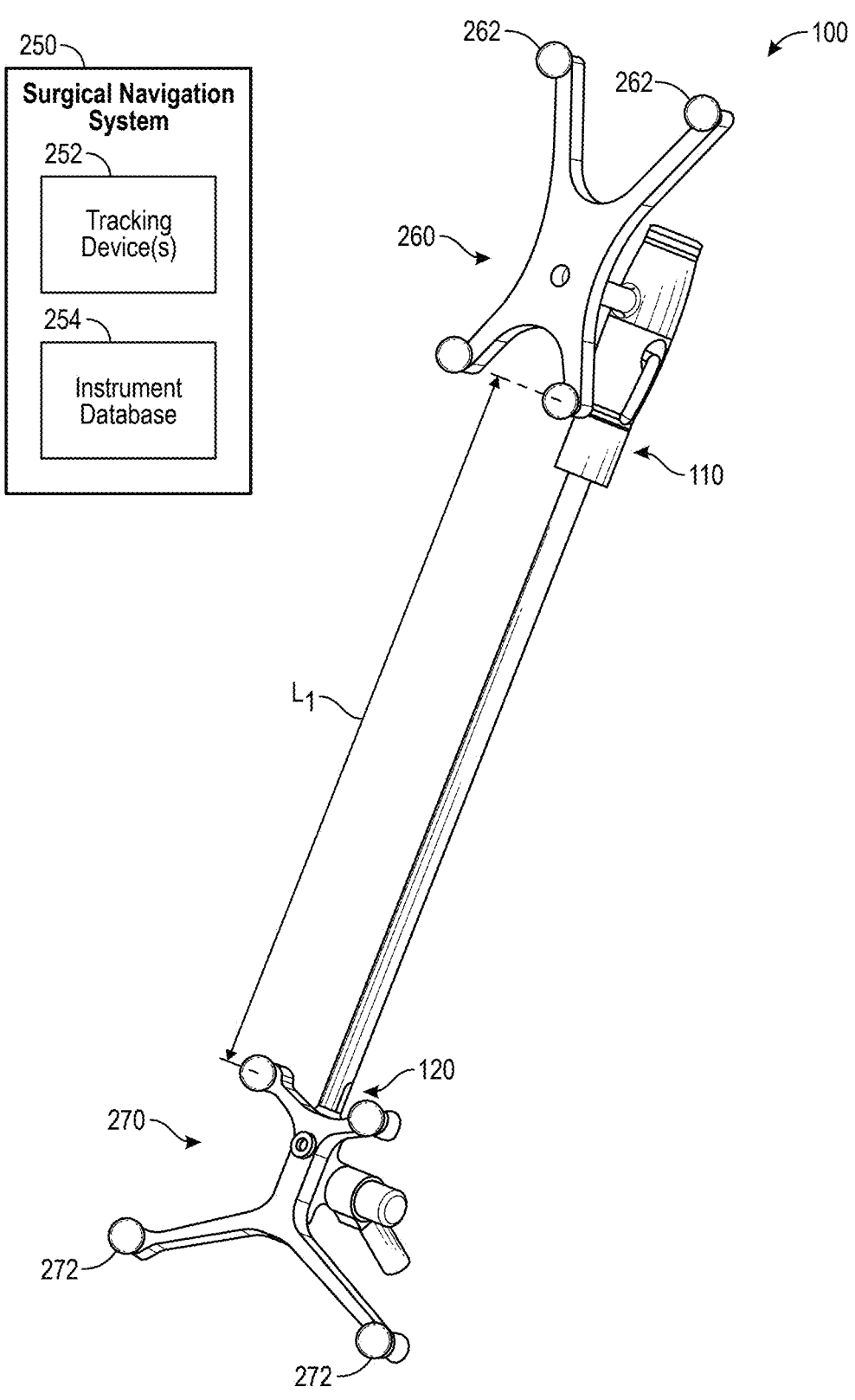
FIG. 2A illustrates the inserter instrument of FIGS. 1A-1E coupled to a patient array with fiducial markers for registering the inserter instrument to a navigation system and configured in accordance with embodiments of the present technology.

In some embodiments, the instrument 100 can be configured for use with "off-the-shelf" or existing surgical navigation systems (e.g., the StealthStation S8 System by Medtronic; Minneapolis, MN) to provide a surgeon and/or other healthcare provider with navigation during a surgical implant procedure using the instrument 100. FIG. 2A illustrates the instrument 100 during a registration process with a surgical navigation system 250 (shown schematically). As shown, the surgical navigation system 250 can include one or more tracking devices 252 which can include optical tracking devices and/or electromagnetic tracking devices. Examples of suitable tracking devices include, but are not limited to, cameras, magnetic resonance imaging (MRI), computed tomography (CT), fluoroscopy imaging, radiofrequency or other electromagnetic transmitters, and/or other intraoperative imaging or location techniques. In operation, the tracking devices 252 can be used to map (e.g., register) one or more pre-operative scans of patient anatomy with a spatial orientation of a patient within an operating room. The tracking devices 252 can also be used to track a position of one or more surgical instruments after the one or more surgical instruments have been registered to the system 250.

The system 250 can further include an instrument database 254, which can include a digital database of known surgical instruments and their precise dimensions. For example, the instrument database may include a digital inventory of specific surgical instruments manufactured by the same company as the surgical navigation system, or specifically designed for use with the surgical navigation system. During registration, a user selects a particular instrument they intend to use during the surgical procedure from digital inventory stored on the instrument database 254. The user then registers the physical instrument corresponding to the selected digital instrument using the tracking devices 252 and one or more fiducial markers on the physical instrument. Because the system 250 knows the exact dimensions of the selected instrument, the system 250 can then track the exact three-dimensional position of the registered instrument using the tracking devices 250 and the fiducial markers on the instrument. In some embodiments, a user can select a registration program from the instrument database 254, which may include a particular surgical instrument, dimensions associated with the particular surgical instrument, instructions for completing registration of the particular surgical instrument, etc.

In some circumstances, the instrument database 254 may not include a surgical instrument that a user wishes to use during an operation. For example, a user may wish to use the surgical navigation system 250 to track the location of instruments manufactured by companies other than the company that manufactured the surgical navigation system 250. The instrument 100 is expected to enable a user to nevertheless register the instrument 100 to the surgical navigation system 250, even in embodiments in which the instrument 100 is not included within the digital inventory in the instrument database 254. For example, to register the instrument 100 to the surgical navigation system 250 in embodiments in which the instrument database 254 does not include the instrument 100, a user can optionally select an instrument from the instrument database 254 that most closely approximates the dimensions of the inserter instrument 100. In a particular embodiment, the user can select an instrument from the instrument database 254 that most closely approximates the dimensions of the inserter instrument 100 when the inserter instrument 100 is in the registration configuration (i.e., when the implant coupling element 120 is flush with, or positioned proximally of, the distal end 115$b_1$ of the shaft 115 as described with reference to FIGS. 1A-1D). For example, the user may select an instrument that has a length that is the same as, or substantially the same as, the first length $L_1$ of the shaft 115. In some embodiments, the system 250 can verify the selected reference instrument from the instrument database 254 based on one or more matching criteria. The matching criteria can be based on user inputted criteria, criteria from the manufacture, machine-learning modules, or the like. The system 250 can also modify registration data (e.g., stored instrument profile) from the instrument database 254 based on, for example, user input, matching corrects, etc. The system 250 can generate a matching score for the reference instrument (e.g., based on matching to a profile of the reference instrument) in the instrument database 254 and notify the user when a threshold matching score has been reached. A user can select another instrument or can modify the procedure. In some embodiments, the inserter instrument 100 may be manufactured to have a dimension (e.g., length) in the registration configuration that is the same or substantially the same as a length of a stored instrument profile in the surgical navigation system 250 such that it can be registered to the system 250 using the profile of a different instrument.

After a particular digital instrument or registration program has been selected, the inserter instrument 100 can be registered to the surgical navigation system 250. To do so, a first reference array or tracker 260 having a plurality of first fiducial markers 262 (only two are labeled in FIG. 2A) can be coupled to the proximal complex 110 of the instrument 100, and a second reference array or tracker 270 having a plurality of second fiducial markers 272 (only two are labeled in FIG. 2A) can be coupled to the distal complex 120 of the instrument 100. The instrument 100 can be registered to the system 250 by using the tracking devices 252 to determine the precise three-dimensional spatial orientation between the first reference array 260 and the second reference array. Of note, however, and as described in detail below with reference to FIGS. 2B and 2C, the instrument 100 is registered to the surgical navigation system 250 when the distal complex 120 is in the second (retracted) configuration. Accordingly, the surgical navigation system 250 registers the first length $L_1$ as the overall length of the shaft 115 (the first length $L_1$ can therefore also be referred to as a "registration length"). In this way, the surgical navigation system 250 recognizes the distal end of the shaft 115 (FIGS. 1C and 1D) as the distal end of the instrument 100, e.g., instead of the distal end 123a of the threaded region 123.

Figure 2B:
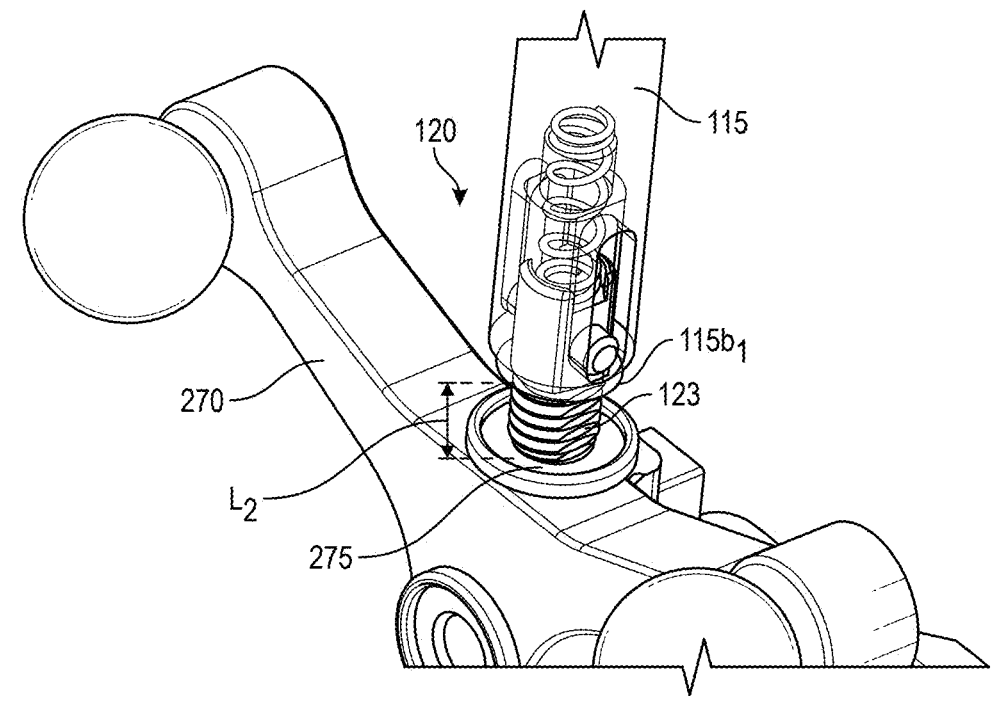
FIG. 2B is an enlarged view of the distal complex of the inserter instrument coupled to the patient array in a first configuration.
Figure 2C:
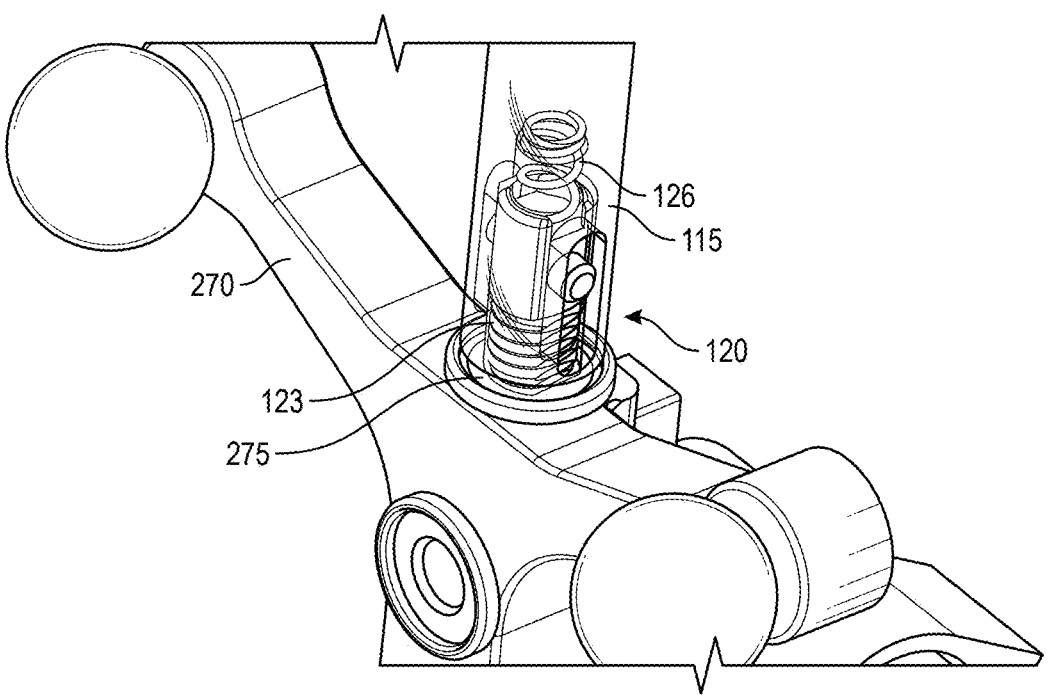
FIG. 2C is an enlarged view of the distal complex of the inserter instrument coupled to the patient array in a second configuration.

FIGS. 2B and 2C are enlarged views of a portion of the instrument 100 including the distal complex 120 and a portion of the second reference array 270. FIG. 2C illustrates the distal complex 120 in the first (delivery) configuration and FIG. 2C illustrates the distal complex 120 in the second (registration) configuration. Referring first to FIG. 2B, with the distal complex 120 in the first configuration, the threaded region 123 extends past the distal end 115b1 of the shaft 115 by the second length $L_2$, as previously described. As a result, a contact surface 275 of the second reference array 270 is also spaced apart from the distal end 115b1 of the shaft 115 by the second length $L_2$. Accordingly, if the instrument 100 were registered with the distal complex 120 in the first (delivery) configuration, the system 250 would register the distal end 123a (FIGS. 1C and 1D) of the threaded region 123 as the distal most portion of the instrument 100, instead of the distal end 115b1 of the shaft 115. Without intending to be bound by theory, registering the distal end 123a of the threaded region 123 as the distal end of the instrument 100 would result in an inaccurate registration of the instrument 100 because, when an implant is coupled to the instrument, the threaded region 123 is inserted into a corresponding hole in the implant such that the implant sits flush against the distal end 115b1 of the shaft 115, as described above with reference to FIGS. 2B and 2C.

Accordingly, to provide accurate registration of the instrument 100, the distal complex 120 can be transitioned to the second (retracted) configuration during the registration process, as shown in FIG. 2C. In the second configuration, the threaded region 123 is retracted into the lumen 117 (by compressing the spring 126) until the distal end 123b (FIGS. 1C and 1D) of the threaded region 123 is flush with, or positioned proximally of, the distal end 115b_1 (FIG. 2B) of the shaft 115. In embodiments in which the threaded region 123 is partially inserted into a corresponding hole in the second reference array 270, the distal complex 120 can be transitioned toward the second position until the contact surface 275 of the second reference array 270 is flush with the distal end 115b_1 of the shaft 115. Regardless, by registering the instrument 100 when the distal complex 120 is in the second (retracted) configuration, the system 250 can register the distal end 115b_1 of the shaft 115 as the distal most portion of the instrument 100, instead of the distal end 123a of the threaded region 123. This is expected to provide accurate registration of the instrument 100 because, as set forth above, the instrument 100 is configured such that the implant sits flush or substantially flush against the distal end 115b_1 of the shaft 115 when coupled to the instrument 100.

After the instrument 100 has been registered, the second reference array 270 can be removed and the threaded region 123 can once again extend distal to the shaft 115. An implant (e.g., the implant 140 of FIG. 1E) can then be screwed onto the threaded region 123 until it sits flush against the distal end 115b_1 of the shaft 115. The surgical navigation system 250 can then track the precise three-dimensional location and orientation of the inserter instrument 100 and/or the implant 140 by virtue of continuing to track the first reference array 260 and using the predetermined spatial orientation between the first reference array 260 and the distal end 115b_1 of the shaft 115.

In some embodiments, the surgical navigation system 250 can use image processing, pattern recognition, and/or machine learning algorithms to track the position the inserter instrument 100 and the implant 140 relative to the patient. The surgical navigation system can display the position of the inserter instrument 100 and/or implant 140 relative to the patient's anatomy. In some embodiments, the surgical navigation system 250 displays a digital version of the inserter instrument 100, a schematic representation of the inserter instrument 100, a digital version of a similar instrument, and/or the implant 140 relative to patient anatomy based on the registration information, pre-operative images, and/or intraoperative images. The physician can therefore track movement of the inserter instrument 100 and precisely navigate through the surgical field, guided by visual cues provided by the surgical navigation system 250. In some embodiments, the surgical navigation system 250 overlays the virtual representation of the inserter instrument 100 onto intraoperative images so that the physician can visualize the instrument's position relative to the patient's anatomy in real-time. This visual feedback assists the physician in accurately guiding and positioning the instrument and/or medical implant during the surgical procedure, thereby enhancing precision and reducing the risk of mispositioning.

Figure 3A:
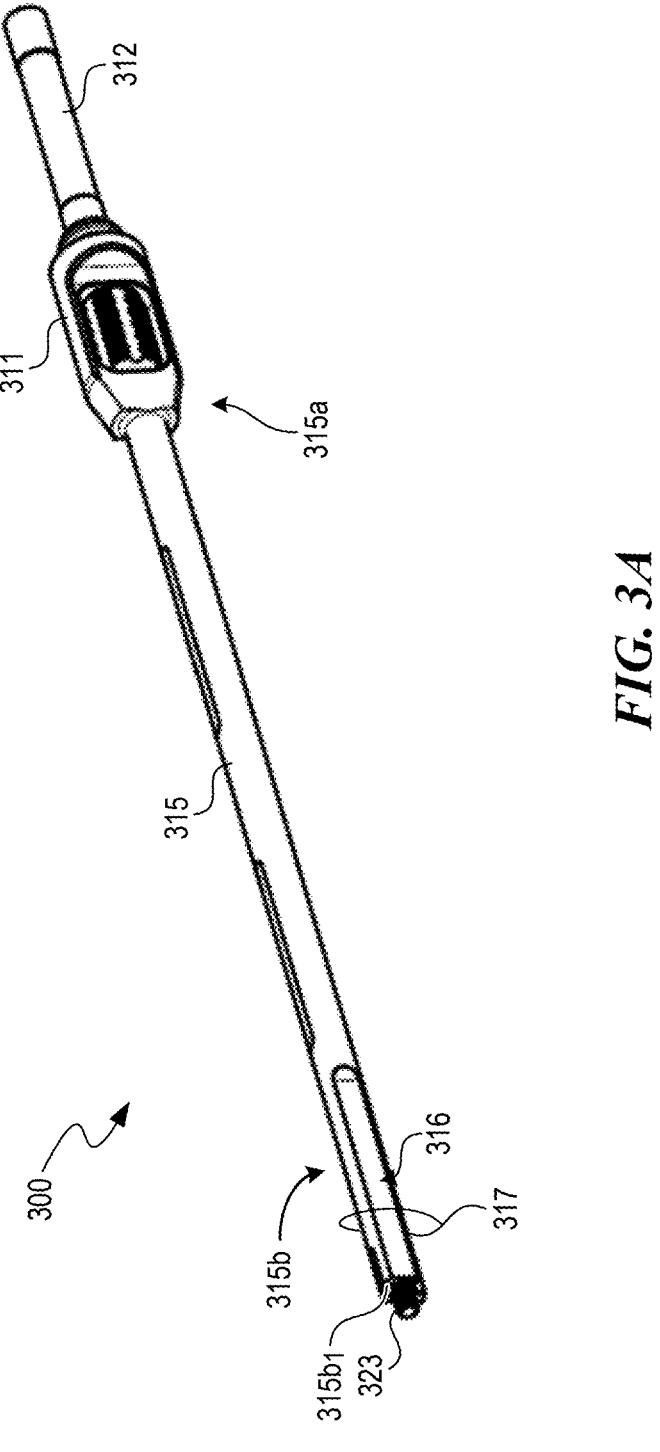
FIG. 3A is an isometric view of another inserter instrument configured in accordance with embodiments of the present technology.
Figure 3B:
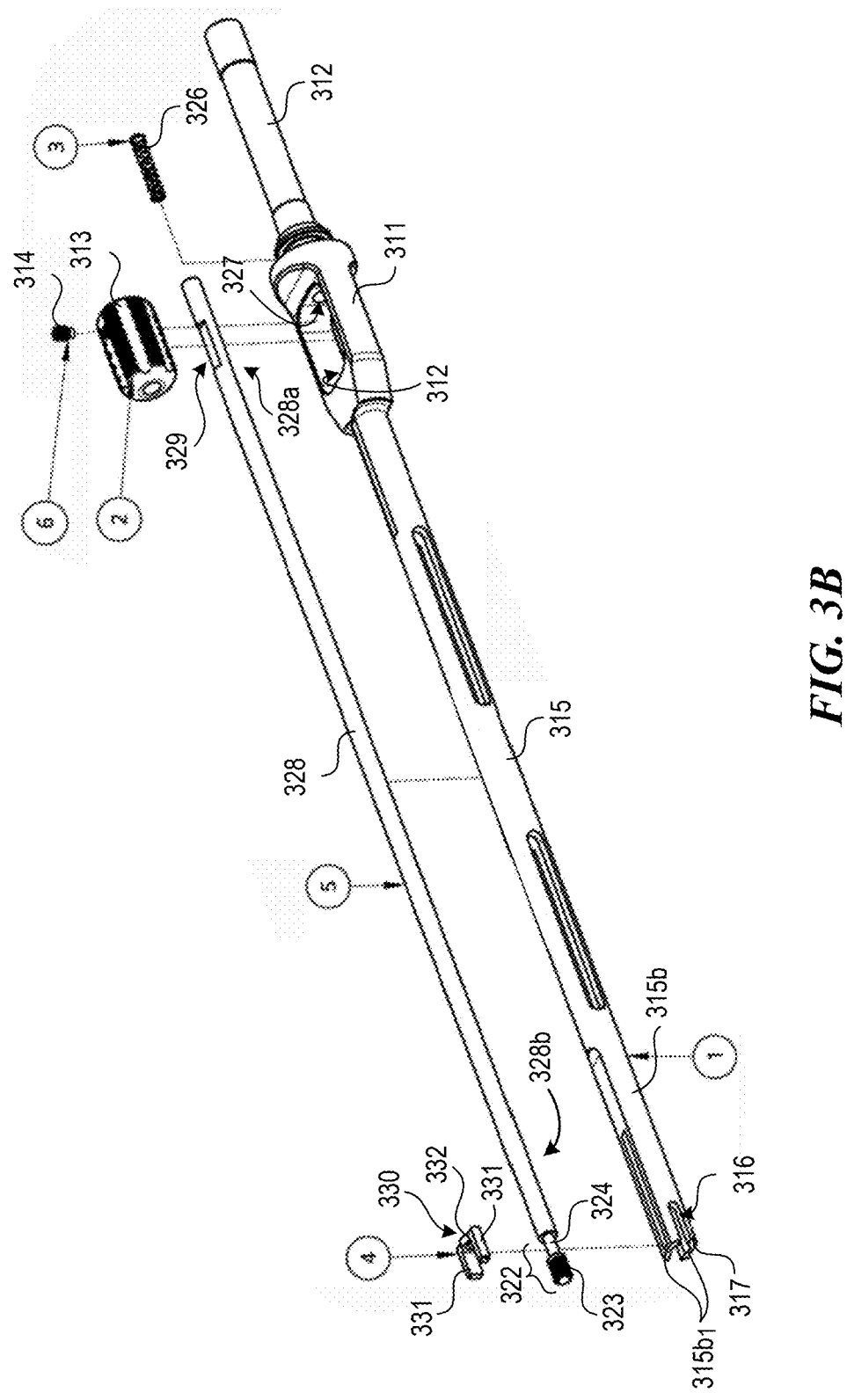
FIG. 3B is an exploded view of the inserter instrument of FIG. 3A.
Figure 3C:
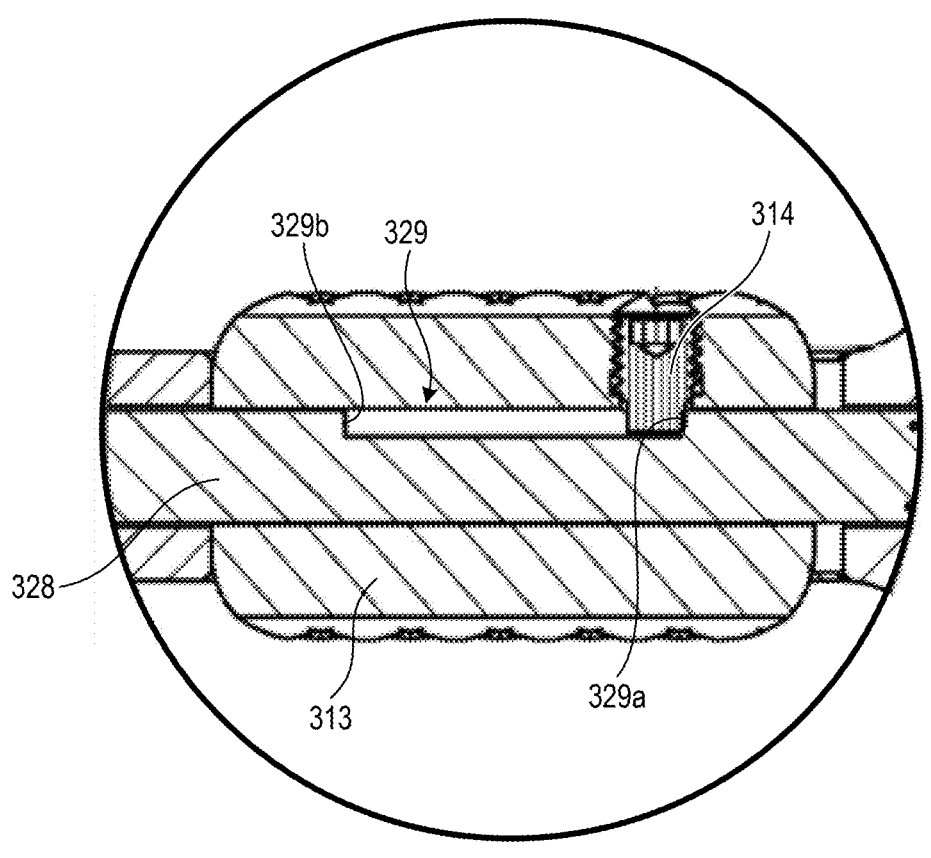
FIG. 3C is an enlarged cross-sectional view of a proximal portion of the inserter instrument of FIG. 3A.

FIGS. 3A-3C illustrate another inserter instrument 300 ("the instrument 300") configured in accordance with embodiments of the present technology. Similar to the instrument 100 described with reference to FIGS. 1A-2C, the instrument 300 can be used to deliver, position, and/or deploy a medical implant at a target implant location within a patient. Also similar to the instrument 100 of FIGS. 1A-2C, the instrument 300 can be transitionable between a first configuration in which it can be releasably coupled to a medical implant, and a second configuration in which it can be accurately registered to a surgical navigation system.

Referring collectively to FIGS. 3A and 3B, which provide an isometric view of the instrument 300 and an exploded view of the instrument 100, respectively, the instrument 300 includes a first shaft 315 (also referred to as "the outer shaft 315") extending between a proximal end portion 315a and a distal end portion 315b. A housing 311 and a handle 312 extend proximally from the proximal end portion 315a of the outer shaft 315. The distal end portion 315b of the outer shaft includes a plurality of tines 317 defining a plurality of slots 316 therebetween.

As best shown in FIG. 3B, the instrument 300 further includes a second shaft 328 (also referred to as "the inner shaft 328") that also extends between a first, proximal end region 328a and a second, distal end region 328b. The inner shaft 328 is sized and shaped to be positioned inside of and coaxial with the outer shaft 315. Accordingly, the inner shaft 328 has an outer diameter that is at least slightly less than an inner diameter of the outer shaft 315. In some embodiments, the inner shaft 328 can translate relative to the outer shaft 315. As described in detail below, this enables a user to transition the instrument 100 between the first (e.g., delivery) configuration and the second (e.g., registration) configuration. The inner shaft 328 can further include a slot 329 at the proximal end region 328a.

With continued reference to FIG. 3B, the instrument 300 further includes an implant coupling element 322 that can be releasably coupled to a medical implant (not shown). The implant coupling element 322 extends from the distal end region 328b of the inner shaft 328. As shown, the implant coupling element 322 includes a threaded region 323 and a base 324, similar to the implant coupling element 122 of FIGS. 1A-2C. However, in the illustrated embodiment the base 324 is a narrow neck region that extends between the threaded region 323 and the inner shaft 328. As best shown in FIG. 3A, when the instrument 300 is in the first (delivery) configuration, at least a portion of the threaded region 323 extends distally out of an end 315$b_1$ of the outer shaft 315 defined by the tines 317, exposing the threaded region 323 for coupling to an implant. The distance the threaded region 323 extends past the distal end 315$b_1$ of the outer shaft 315 can be based at least in part on a depth of a corresponding threaded female coupling element of a medical implant (not shown), and can have any of the second lengths $L_2$ described above with reference to the instrument 100 of FIGS. 1A-2C.

Returning to FIG. 3B, in some embodiments, the instrument 300 can further include a positioning element 330 having (a) an opening 332 sized and shaped to receive the base 324 of the implant coupling element 322, and (b) a pair of arms 331 sized and shape to extend parallel to the implant coupling element 322. When the instrument 300 is assembled, the arms 331 can reside within the slots 316 formed in the outer shaft 315, and the inner shaft 328 can rotate relative to the positioning element 330. In some embodiments, each arm 331 can have a different width, height, shape, etc. In operation, the arms 331 can mate with an implant (not shown) coupled to the implant coupling element 322 to provide rotational control and/or steering of the implant during a surgical procedure. For example, the asymmetrical arms 331 provide rotational and/or positional control to assist with deploying the implant in the correct orientation.

Similar to the instrument 100 of FIGS. 1A-2C, the instrument 300 can further include a spring 326. However, unlike the instrument 100 of FIGS. 1A-2C, the spring 326 is positioned at a proximal end of the instrument 300. In particular, the spring 326 can be sized and shaped to fit within a corresponding spring aperture or channel 327 that extends within the handle 312 proximal to the inner shaft 328. The spring 326 can provide a similar biasing mechanism that enables the implant coupling element 322 to be selectively transitioned between a first configuration in which the threaded portion 423 extends distally from the outer shaft 315 (e.g., for implant coupling and delivery, as shown in FIG. 3A), and a second configuration in which the threaded region 323 is flush with or recessed within the outer shaft 315 (e.g., for registration of the instrument 300, not shown in FIG. 3A or 3B). For example, the spring 326 can bias the inner shaft 328 toward the first configuration, but can be compressed in response to a proximally directed force that causes the inner shaft 328 to translate proximally relative to the outer shaft 315 and the implant coupling element 322 to retract within the outer shaft 315.

The instrument 300 can also include a knob 313 and a pin 314. As best shown in FIG. 3C, which is an enlarged cross-sectional view of a portion of the instrument including the knob 313 and the pin 314, the knob 313 can be positioned around the inner shaft 328 and within the housing 311. The pin 314 can extend at least partially through the knob 313 such that the pin 314 is slidably received within the slot 329 formed within the inner shaft 328. The pin 314 and slot 329 can together define a range of motion for the axial translation of the inner shaft 328. For example, when the implant coupling element 322 is retracted into the outer shaft 315, the inner shaft 328 can be translate proximally until a distal edge 329b of the slot 329 contacts the pin 314. Likewise, when the implant coupling element 322 extends distally out of the outer shaft 315, the inner shaft 328 can translate distally until a proximal edge 329a of the slot 329 contacts the pin 314. In some embodiments, the range axial motion of the inner shaft 328 can be controlled through other mechanisms (such as via the spring 326), in addition to or in lieu of being controlled by the pin 314 and the slot 329. In some embodiments, the pin 314 and the slot 239 may additionally reduce or prevent rotation of the inner shaft 328 relative to the outer shaft 315, e.g., by rotationally keying the inner shaft 328 to the outer shaft 315.

Figure 4:
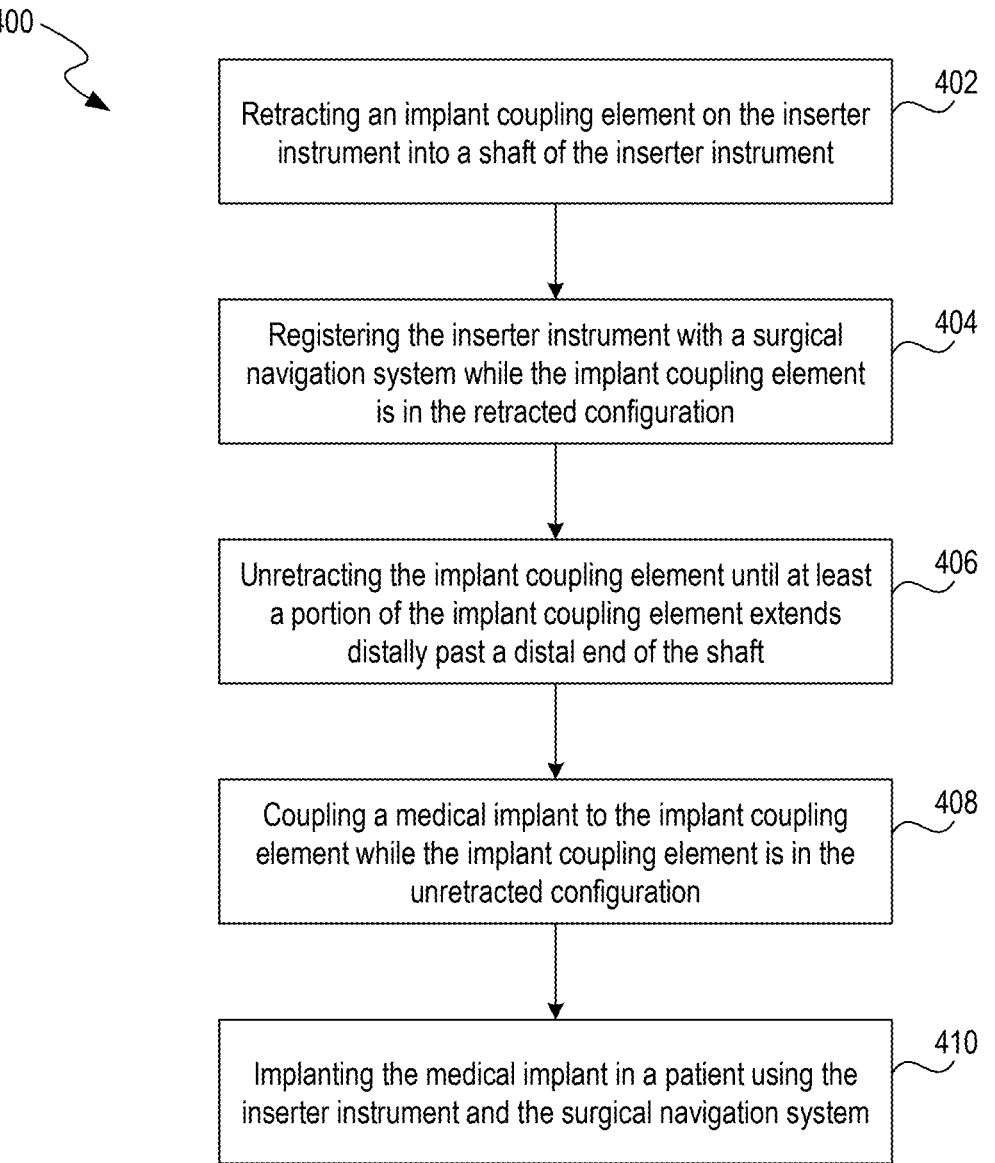
FIG. 4 is a flowchart of a method of registering an inserter instrument with a surgical navigation system in accordance with select embodiments of the present technology.

The present technology can further include methods of registering an inserter instrument to a surgical navigation system. For example, FIG. 4 is a flowchart illustrating a method 400 of registering an inserter instrument to a medical device in accordance with embodiments of the present technology. As one skilled in the art will appreciate, the method 400 can be performed using the inserter instrument 100 of FIGS. 1A-2C, the inserter instrument 300 of FIG. 3A-3C, or other similar inserter instruments having a retractable tip.

The method 400 can begin at block 402 by retracting an implant coupling element on the inserter instrument into a shaft of the inserter instrument. In some embodiments, this includes retracting the implant coupling element until a distal end of the implant coupling element is even with, or positioned proximally of, a distal end of the shaft, such that the distal end of the shaft represents the distal-most end of the inserter instrument. In some embodiments, the operation at block 402 can be performed by manually providing a proximally-directed force against the implant coupling element. In other embodiments, the operation at block 402 can be performed by toggling an actuator or other mechanism that causes the implant coupling element to retract into the shaft. Regardless, the operation at block 402 is typically performed before a medical implant has been coupled to the implant coupling element.

The method 400 can continue at block 404 by registering the inserter instrument with a surgical navigation system while the implant coupling element is in the retracted configuration. In some embodiments, the operation at block 404 includes selecting, from a digital database of instruments stored on the surgical navigation system, a particular instrument profile that has generally similar dimensions as the inserter instrument. For example, the operation at block 404 can include selecting a particular instrument profile that has dimensions that are the same as, or generally similar to, the dimensions of the inserter instrument when the inserter instrument is in the registration configuration. In other embodiments, the operation at block 404 includes selecting the inserter instrument itself from the digital database of instruments. Registration can then be performed by establishing a three-dimensional spatial orientation between one or more tracking devices (e.g., imaging devices, electromagnetic devices, etc.) of the surgical navigation system and the inserter instrument, in accordance with techniques known in the art that will depend on the specific model of the surgical navigation system being used. Of note, however, and as described in detail throughout this Detailed Description, registering the inserter instrument with the implant coupling element in the retracted configuration is expected to cause the surgical navigation system to register the distal end of the shaft, as opposed to the distal end of the implant coupling element, as the distal-most portion of the inserter instrument.

The method 400 can continue at block 406 by, after registration is complete, unretracting the implant coupling element until at least a portion of the implant coupling element extends distally past the distal end of the shaft. This exposes the implant coupling element for coupling to a medical implant. In some embodiments, the operation at block 406 can be performed simply by removing the proximally directed force being applied to the implant coupling element (e.g., in embodiments in which the implant coupling element is biased toward the un-retracted state). In other embodiment, the operation at block 406 can be performed by toggling an actuator or other mechanism that unretracts the implant coupling element. Regardless, the surgical navigation system 100 will recognize the distal end of the shaft, and not the distal end of the implant coupling element, as the distal end of the inserter instrument even after the implant coupling element has been unretracted.

With the implant coupling element exposed, the method 400 can continue at block 408 by coupling a medical implant to the implant coupling element while the implant coupling element is in the unretracted configuration. In some embodiments, this may include threading the medical implant onto a threaded portion of the implant coupling element until the medical implant is flush with the distal end of the shaft. The method 400 can continue at block 410 by implanting the medical implant in a patient using the inserter instrument and the surgical navigation system.

CONCLUSION

As one skilled in the art will appreciate, any of the software modules described previously may be combined into a single software module for performing the operations described herein. Likewise, the software modules can be distributed across any combination of the computing systems and devices described herein, and are not limited to the express arrangements described herein. Accordingly, any of the operations described herein can be performed by any of the computing devices or systems described herein, unless expressly noted otherwise.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable" to each other to achieve the desired functionality. Specific examples of operably couplable include but are not limited to physically mateable and/or physically interacting components and/or wirelessly interactable and/or wirelessly interacting components and/or logically interacting and/or logically interactable components.

The embodiments, features, systems, devices, materials, methods and techniques described herein may, in some embodiments, be similar to any one or more of the embodiments, features, systems, devices, materials, methods and techniques described in the following:

U.S. application Ser. No. 16/048,167, filed on Jul. 27, 2018, titled "SYSTEMS AND METHODS FOR ASSISTING AND AUGMENTING SURGICAL PROCEDURES;"

U.S. application Ser. No. 16/242,877, filed on Jan. 8, 2019, titled "SYSTEMS AND METHODS OF ASSISTING A SURGEON WITH SCREW PLACEMENT DURING SPINAL SURGERY;"

U.S. application Ser. No. 16/207,116, filed on Dec. 1, 2018, titled "SYSTEMS AND METHODS FOR MULTI-PLANAR ORTHOPEDIC ALIGNMENT;"

U.S. application Ser. No. 16/352,699, filed on Mar. 13, 2019, titled "SYSTEMS AND METHODS FOR ORTHOPEDIC IMPLANT FIXATION;"

U.S. application Ser. No. 16/383,215, filed on Apr. 12, 2019, titled "SYSTEMS AND METHODS FOR ORTHOPEDIC IMPLANT FIXATION;"

U.S. application Ser. No. 16/569,494, filed on Sep. 12, 2019, titled "SYSTEMS AND METHODS FOR ORTHOPEDIC IMPLANTS;" and U.S. application Ser. No. 16/699,447, filed Nov. 29, 2019, titled "SYSTEMS AND METHODS FOR ORTHOPEDIC IMPLANTS;"

U.S. application Ser. No. 16/735,222, filed Jan. 6, 2020, titled "PATIENT-SPECIFIC MEDICAL PROCEDURES AND DEVICES, AND ASSOCIATED SYSTEMS AND METHODS;"

U.S. application Ser. No. 16/987,113, filed Aug. 6, 2020, titled "PATIENT-SPECIFIC ARTIFICIAL DISCS, IMPLANTS AND ASSOCIATED SYSTEMS AND METHODS;"

U.S. application Ser. No. 16/990,810, filed Aug. 11, 2020, titled "LINKING PATIENT-SPECIFIC MEDICAL DEVICES WITH PATIENT-SPECIFIC DATA, AND ASSOCIATED SYSTEMS, DEVICES, AND METHODS;"

U.S. application Ser. No. 17/085,564, filed Oct. 30, 2020, titled "SYSTEMS AND METHODS FOR DESIGNING ORTHOPEDIC IMPLANTS BASED ON TISSUE CHARACTERISTICS;"

U.S. application Ser. No. 17/100,396, filed Nov. 20, 2020, titled "PATIENT-SPECIFIC VERTEBRAL IMPLANTS WITH POSITIONING FEATURES;"

U.S. application Ser. No. 17/342,439, filed Jun. 8, 2021, titled "PATIENT-SPECIFIC MEDICAL PROCEDURES AND DEVICES, AND ASSOCIATED SYSTEMS AND METHODS;"

U.S. application Ser. No. 17/463,054, filed Aug. 31, 2021, titled "BLOCKCHAIN MANAGED MEDICAL IMPLANTS;"

U.S. application Ser. No. 17/518,524, filed Nov. 3, 2021, titled "PATIENT-SPECIFIC ARTHROPLASTY DEVICES AND ASSOCIATED SYSTEMS AND METHODS;"

U.S. application Ser. No. 17/531,417, filed Nov. 19, 2021, titled "PATIENT-SPECIFIC JIG FOR PERSONALIZED SURGERY;"

U.S. application Ser. No. 17/678,874, filed Feb. 23, 2022, titled "NON-FUNGIBLE TOKEN SYSTEMS AND METHODS FOR STORING AND ACCESSING HEALTHCARE DATA;"

U.S. application Ser. No. 17/835,777, filed Jun. 8, 2022, titled "PATIENT-SPECIFIC EXPANDABLE INTERVERTEBRAL IMPLANTS;"

16

U.S. application Ser. No. 17/842,242, filed Jun. 16, 2022, titled "PATIENT-SPECIFIC ANTERIOR PLATE IMPLANTS;"

U.S. application Ser. No. 17/851,487, filed Jun. 28, 2022, titled "PATIENT-SPECIFIC ADJUSTMENT OF SPINAL IMPLANTS, AND ASSOCIATED SYSTEMS AND METHODS;"

U.S. application Ser. No. 17/856,625, filed Jul. 1, 2022, titled "SPINAL IMPLANTS FOR MESH NETWORKS;"

U.S. application Ser. No. 17/867,621, filed Jul. 18, 2022, titled "PATIENT-SPECIFIC SACROILIAC IMPLANT, AND ASSOCIATED SYSTEMS AND METHODS;"

U.S. application Ser. No. 17/868,729, filed Jul. 19, 2022, titled "SYSTEMS FOR PREDICTING INTRAOPERATIVE PATIENT MOBILITY AND IDENTIFYING MOBILITY-RELATED SURGICAL STEPS;"

U.S. application Ser. No. 17/951,085, filed Sep. 22, 2022, titled "SYSTEMS FOR MANUFACTURING AND PRE-OPERATIVE INSPECTING OF PATIENT-SPECIFIC IMPLANTS;"

U.S. application Ser. No. 17/978,673, filed Nov. 1, 2022, titled "SPINAL IMPLANTS AND SURGICAL PROCEDURES WITH REDUCED SUBSIDENCE, AND ASSOCIATED SYSTEMS AND METHODS;"

U.S. application Ser. No. 17/978,746, filed Nov. 1, 2022, titled "PATIENT-SPECIFIC SPINAL INSTRUMENTS FOR IMPLANTING IMPLANTS AND DECOMPRESSION PROCEDURES;"

U.S. application Ser. No. 18/102,444, filed Jan. 27, 2023, titled "TECHNIQUES TO MAP THREE-DIMENSIONAL HUMAN ANATOMY DATA TO TWO-DIMENSIONAL HUMAN ANATOMY DATA;"

U.S. application Ser. No. 18/113,573, filed Feb. 24, 2023, titled "PATIENT-SPECIFIC IMPLANT DESIGN AND MANUFACTURING SYSTEM WITH A DIGITAL FILING CABINET;"

U.S. application Ser. No. 18/120,979, filed Mar. 13, 2023, titled "MULTI-STAGE PATIENT-SPECIFIC SURGICAL PLANS AND SYSTEMS AND METHODS FOR CREATING AND IMPLEMENTING THE SAME;"

U.S. application Ser. No. 18/455,881, filed Aug. 25, 2023, titled "SYSTEMS AND METHODS FOR GENERATING MULTIPLE PATIENT-SPECIFIC SURGICAL PLANS AND MANUFACTURING PATIENT-SPECIFIC IMPLANTS;"

U.S. application Ser. No. 18/384,762, filed Oct. 28, 2023, titled "SYSTEMS AND METHODS FOR SELECTING, REVIEWING, MODIFYING, AND/OR APPROVING SURGICAL PLANS;"

U.S. application Ser. No. 18/537,600, filed Dec. 12, 2023, titled "PATIENT-SPECIFIC IMPLANT DESIGN AND MANUFACTURING SYSTEM WITH A REGULATORY AND REIMBURSEMENT MANAGER;"

International Application No. PCT/US24/10202, filed Jan. 3, 2024, titled "PATIENT-SPECIFIC SPINAL FUSION DEVICES AND ASSOCIATED SYSTEMS AND METHODS;"

U.S. application Ser. No. 18/408,409, filed Jan. 9, 2024, titled "SYSTEM FOR EDGE CASE PATHOLOGY IDENTIFICATION AND IMPLANT MANUFACTURING;"

U.S. application Ser. No. 18/408,452, filed Jan. 9, 2024, titled "SYSTEM FOR MODELING PATIENT SPINAL CHANGES;"

U.S. application Ser. No. 18/415,577, filed Jan. 17, 2024, titled "PATIENT-SPECIFIC IMPLANT DESIGN AND MANUFACTURING SYSTEM WITH A SURGICAL IMPLANT POSITIONING MANAGER;"

U.S. Application No. 63/539,797, filed Sep. 21, 2023, titled "ROTATABLE INTERVERTEBRAL IMPLANTS FOR TRANSFORAMINAL LUMBAR INTERBODY FUSION TECHNIQUES;" and U.S. Application No. 63/542,264, filed Oct. 3, 2023, titled "PATIENT-SPECIFIC SURGICAL POSITIONING GUIDES AND METHODS OF MAKING AND USING THE SAME."

All of the above-identified patents and applications are incorporated by reference in their entireties. In addition, the embodiments, features, systems, devices, materials, methods and techniques described herein may, in certain embodiments, be applied to or used in connection with any one or more of the embodiments, features, systems, devices, or other matter.

The ranges disclosed herein also encompass any and all overlap, sub-ranges, and combinations thereof. Language such as "up to," "at least," "greater than," "less than," "between," or the like includes the number recited. Numbers preceded by a term such as "approximately," "about," and "substantially" as used herein include the recited numbers (e.g., about 10%=10%), and also represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A method of registering an inserter instrument having a retractable implant coupling element to a surgical navigation system, the method comprising:

retracting the implant coupling element into a shaft of the inserter instrument until a distal end of the implant coupling element is even with or positioned proximally of a distal end of the shaft;

registering the inserter instrument with a surgical navigation system while the implant coupling element is even with or positioned proximally of the distal end of the shaft;

after registering the inserter instrument, unretracting the implant coupling element until at least a portion of the implant coupling element extends distally of the distal end of the shaft; and coupling a medical implant to the portion of the implant coupling element that extends distally of the distal end of the shaft.

2. The method of claim 1 wherein retracting the implant coupling element includes pushing the implant coupling element into the shaft.

3. The method of claim 1 wherein retracting the implant coupling element includes compressing a spring within the inserter instrument.

4. The method of claim 1 wherein retracting the implant coupling element includes slidably translating the implant coupling element relative to the shaft.

5. The method of claim 1 wherein registering the inserter instrument includes registering the inserter instrument such that the surgical navigation system tracks a position of the distal end of the shaft independent of a position of the implant coupling element relative to the shaft.

6. The method of claim 1 wherein registering the inserter instrument includes selecting, from a digital database storing a plurality of instrument profiles, a specific instrument profile similar to, but not the same as, the inserter instrument.

7. The method of claim 1 wherein registering the inserter instrument includes selecting a registration program of the surgical navigation system based on a profile of the inserter instrument when the implant coupling element is even with or positioned proximally of the distal end of the shaft, and wherein the surgical navigation system is programmed to use the selected registration program to register the inserter instrument in the registration configuration.

8. The method of claim 1, further comprising intraoperatively tracking a position of the inserter instrument and/or the medical implant relative to a patient during a surgical procedure to implant the medical implant into the patient.

9. The method of claim 8 wherein the intraoperatively tracking the position of the inserter instrument includes intraoperatively tracking the position of the distal end of the shaft independent of a position of the implant coupling element relative to the shaft.

10. The method of claim 1 wherein the shaft defines a visualizable profile configured to be identifiable by the surgical navigation system when the implant coupling element is even with or positioned proximally of the distal end of the shaft, wherein the medical implant is configured to allow the surgical navigation system to track the visualizable profile while the medical implant is connected to the inserted instrument.

11. The method of claim 1, wherein the surgical navigation system is programmed to intraoperatively track a position and orientation of the inserter instrument in three-dimensions after the inserter instrument is registered thereto.

* * * * *